United States Patent [19]

Klein et al.

[11] Patent Number: 4,505,860
[45] Date of Patent: Mar. 19, 1985

[54] CYCLIC KETO-BUTYRALDEHYDES A PROCESS FOR THEIR PREPARATION, AND THEIR USE IN THE PREPARATION OF CYCLIC DIISOCYANATES

[75] Inventors: Gerhard Klein, Monheim; Dieter Arlt, Cologne; Rudolf Braden, Odenthal, all of Fed. Rep. of Germany

[73] Assignee: Bayer Aktiengesellschaft, Leverkusen, Fed. Rep. of Germany

[21] Appl. No.: 410,791

[22] Filed: Aug. 23, 1982

[30] Foreign Application Priority Data

Sep. 10, 1981 [DE] Fed. Rep. of Germany ....... 3135948

[51] Int. Cl.³ .................... C07C 69/00; C08G 18/00; C08G 18/10
[52] U.S. Cl. .................. 260/453 A; 260/453 PH; 564/448; 521/155; 528/75; 528/44
[58] Field of Search ................. 260/453 A, 453 PH; 564/448

[56] References Cited

U.S. PATENT DOCUMENTS 2,692,275 10/1954 Bortnick ................. 260/453 A
3,401,190 9/1968 Schmitt et al. ........... 260/453 A
3,565,954 2/1971 Bouniot .................. 564/448

OTHER PUBLICATIONS

Methoden der Organischen Chemie, (Houben-Weyl) Vierte, Vollig Neu Gestaltete Auglage, Eugen Muller und Otto Bayer, Leverkusen, 1980, (Translation attached).
Patents Abstracts of Japan, Band 3, Nr. 50(C-44), 27., Apr. 1979, Seite 29C44 & JP-A-54 24843 (Mitsubishi Yuka K.K.), 2/24/1979* Zusammenfassung*.

Primary Examiner—Alan Siegel
Attorney, Agent, or Firm—Sprung, Horn, Kramer & Woods

[57] ABSTRACT

New cyclic keto-butyraldehydes of the formula

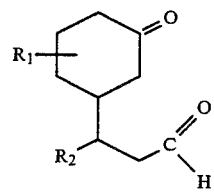

in which
$R_1$ and $R_2$ are either identical or different and denote hydrogen or lower alkyl and in which the cycloaliphatic ring may contain a double bond, can be prepared from the corresponding cyclic keto-olefins in the presence of a rhodium-containing catalyst by reaction with carbon monoxide and hydrogen. The new cyclic keto-butyraldehydes can be used in the preparation of diisocyanates which are used as crosslinking agents in the preparation of polyurethanes.

2 Claims, No Drawings

CYCLIC KETO-BUTYRALDEHYDES A PROCESS FOR THEIR PREPARATION, AND THEIR USE IN THE PREPARATION OF CYCLIC DIISOCYANATES

The invention relates to new cyclic keto-butyraldehydes and their preparation from cyclic keto-olefins The new cyclic keto-butyraldehydes can be used for the preparation of cyclic diisocyanates which can be used as crosslinking agents in polymers.

Final products, in particular in polymer chemistry, are based as a rule on starting materials originating from petroleum. In view of the general scarcity of petroleum products there is a demand, in the development of new products, for starting materials which are independent of petroleum and continuously reform afresh.

The present invention relates to new cyclic keto-butyraldehydes which are derived from hydrocarbons of the limonene type.

The new cyclic keto-butyraldehydes correspond to the formula (I)

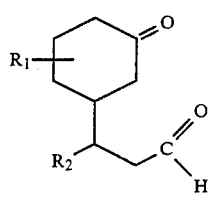

in which
R$_1$ and R$_2$ are either identical or different and denote hydrogen or lower alkyl and in which the cycloaliphatic ring may contain a double bond.

Within the scope of the present invention lower alkyl can be a straight-chain or branched hydrocarbon radical having 1 to about 6 carbon atoms. Examples which may be mentioned are methyl, ethyl, propyl, isopropyl, butyl, isobutyl, pentyl, isopentyl, hexyl and isohexyl.

Cyclic keto-butyraldehydes of the formula (II)

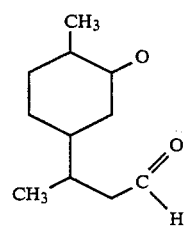

in which
the cycloaliphatic ring may contain a double bond, are in general preferred.

The following cyclic keto-butyraldehydes may be mentioned in particular:
3-[4-methyl-3-oxocyclohexyl]-butyraldehyde, 3-[4-methyl-3-oxocyclohex-4-enyl]-butyraldehyde, 3-[3-oxocyclohexyl]-propionaldehyde and 3-[4-methyl-3-oxocyclohexyl]-propionaldehyde.

The new cyclic keto-butyraldehydes according to the invention can be used as scents, e.g., perfume component. However, it is particularly possible to convert them to the corresponding diamines and the latter into diisocyanates. The cyclic disocyanates can advantageously be used as crosslinking agents in polymer chemistry, in particular in the case of polyamides and polyurethanes.

The new cyclic keto-butyraldehydes can be prepared by reacting cyclic keto-olefins of the formula III

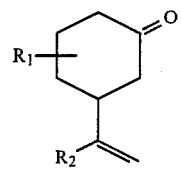

in which
R$_1$ and R$_2$ are either identical or different and denote hydrogen or lower alkyl and in which the cycloaliphatic ring may contain a double bond, in the presence of a rhodium-containing catalyst with carbon monoxide and hydrogen within a temperature range of 50° to 200° C. and under a pressure of at least 30 bar.

Cyclic keto-olefins for the process according to the invention, such as carvone and dihydrocarvone, can be prepared from limonene. Limonene is a constituent of citrus fruits, such as oranges, lemons and limes, and is in general isolated by distillation of fruit peel.

The preparation of carvone from limonene is known. Thus, for example, a dimeric chloronitroso compound can be obtained by the addition of nitrosyl chloride to the endocyclic double bond of limonene. This chloronitroso compound can be converted by means of bases into carvone oxime which can be hydrolyzed under acid conditions to give carvone (Ind. Eng. Chem., 43, 1196 (1951)). This three-stage reaction can also be carried out as a so-called one-vessel process (U.S. Pat. No. 3,293,301).

The preparation of the dihydrocarvone is likewise known. For example, limonene can be converted by means of per acids into limonene monoepoxide (J. Amer. Chem. Soc., 77, 3405 (1955)). This epoxide can be rearranged by means of Lewis acids (Helv. Chim. Acta 47, 413 (1964)) or by means of acid ion exchangers (Za. Vses. Khem. Oesaca. 22, 223 (1977)) to give dihydrocarvone.

The preparation of the cyclic keto-olefins can also be carried out with the aid of a Diels-Alder reaction. In this case, a suitable diene is reacted with isoprene, if appropriate in the presence of a Lewis acid.

The hydroformylation of the cyclic keto-olefins by means of carbon monoxide/hydrogen by the process according to the invention is carried out in the presence of a rhodium catalyst. The hydroformylation of limonene is in itself known (New Synthesis with Carbon Monoxide, Springer Verlag Berlin (1980), pages 109-119). However, it was not to be expected that the known process could be transferred to possibly unsaturated cyclic keto-olefins, since in addition to having two double bonds they are additionally substituted by a keto group which should react preferentially under the reaction conditions.

Preferred rhodium complexes for the process according to the invention contain one or more nitrogen-, phosphorus- and/or sulphur-containing ligands.

Particularly preferred rhodium complexes used as catalysts correspond to the formulae XRh(CO)L$_2$, HRh(CO)L$_3$, HRh(CO)$_2$L$_2$, RhXL$_3$, [Rh(CO)$_2$L$_2$] and [Rh(OCOCH$_3$)(CO)L]$_2$, wherein X represents a chlorine, bromine or iodine atom and L represents an organic ligand. Suitable organic ligands can be tertiary organic phosphines, sulphides, sulphones or tertiary amines. Examples of suitable ligands are tertiary organic phosphines which have, as organic radicals, in each case at most up to two identical or different alkyl radicals having 1 to 20 carbon atoms, cycloalkyl radicals having 5 to 12 carbon atoms, aralkyl radicals having 7 to 10 carbon atoms and at least one aryl radical having 6 to 10 carbon atoms. The radicals mentioned can have substituents which are inert under the reaction conditions, for example 1 to 2 hydroxyl groups, alkoxy or carbalkoxy groups having 1 to 4 carbon atoms, amino groups or halogen atoms, such as triphenylphosphine, diethylphenylphosphine, tritolylphosphine, trinaphthylphosphine, diphenylmethylphosphine, diphenylbutylphosphine, tris-(p-chlorophenyl)-phosphine, tris-(p-carbomethoxyphenyl)-phosphine, tris-(p-cyanophenyl)-phosphine, diphenylphosphonous acid phenyl ester, benzenephosphonous acid diphenyl ester and diphenyl-(dimethylamino)-phenylphosphine.

P[CH$_2$CH$_2$CH$_2$N(CH$_3$)$_2$]$_3$,
P[CH$_2$CH$_2$CH$_2$N(C$_2$H$_5$)$_2$]$_3$,

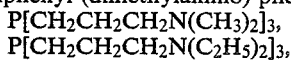

P[CH$_2$CH$_2$CH$_2$N(iso-C$_4$H$_9$)$_2$]$_3$,
(n-C$_4$H$_9$)$_2$PCH$_2$CH$_2$N(C$_2$H$_5$)$_2$,
P[CH$_2$N(C$_2$H$_5$)$_2$]$_3$,
P[C$_6$H$_4$N(CH$_3$)$_2$]$_3$,
P[CH$_2$CH$_2$C$_6$H$_4$N(C$_2$H$_5$)$_2$]$_3$,

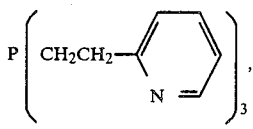

P[CH$_2$CH$_2$CH$_2$N(tert.C$_4$H$_9$)$_2$]$_3$ and
P[CH$_2$CH$_2$CH$_2$N(iso-C$_3$H$_7$)$_2$]$_3$ The phosphorus-containing ligands used are best selected from the group of the phosphines. Particularly preferred ligands are triphenylphosphine and tributylphosphine.

Complex ligands in the form of triorganophosphines which are partially substituted by ferrocene (German Offenlegungsschrift No. 2,617,306) can also be used according to the invention. However, any triorganophosphorus ligand which is suitable for rhodium-catalyzed hydroformylation reaction systems can be used.

Examples of suitable nitrogen-containing ligands are pyridine, picolines, ethylpyridines, N-methylpyrrolidine, N-methylpyrrole, N,N'-dimethylpiperazine, dimethylcyclohexylamine, triethylamine, N,N-dimethylaniline, N-methylmorphidine, N-methylindole, quinoline, isoquinoline, N-methylpyrrolidone and 3-dimethylaminopropionitrile.

Examples of suitable sulphur-containing ligands are dibenzyl sulphide, di-n-butyl sulphide, dimethyl sulphoxide, diethyl sulphide, di-(4-chlorobenzyl)sulphide, di-(4-cyanobenzyl)sulphide, bis-(4-dimethylaminobenzyl)sulphide, di-(4-diethylaminobenzyl)sulphide, di-(α-naphthylmethyl)sulphide, di-(2,6-dichlorobenzyl)sulphide, di-(3,4-dichlorobenzyl)sulphide, di-(2-chlorobenzyl)sulphide, di-(5,6,7,8-tetrahydronaphthyl-2-methyl)sulphide, benzylmethyl sulphide, benzyldodecyl sulphide, 4-dimethylaminobenzylmethyl sulphide, benzylbutyl sulphide, bis-(4-carboxybenzyl)sulphide, di-(4-methylbenzyl)sulphide, di-(3-methylbenzyl)sulphide, di-(2-methylbenzyl)sulphide and tetramethylene sulphone.

In the catalyst complex the quantity ratio of rhodium to ligand can be varied within a wide range. However, in general the reaction medium contains at least one mol of ligand per gram atom of rhodium. But the ligand can also be added in high excess, so that a molar ratio of ligand to rhodium of 1 to 200:1 is employed. However, a molar ratio of ligand to rhodium of 10 to 80:1 is preferably used. It can also be advantageous to use the ligand compound as solvent.

In a preferred embodiment of the process according to the invention, the active catalyst is preformed in a solvent at an elevated temperature and under an elevated pressure, for example under a water gas pressure of 200 bar, and the cyclic keto-olefin is added under the reaction conditions.

1 to 1,000 mg of rhodium metal is employed according to the invention in the catalyst per kg of cyclic keto-olefine. In particular, 10 to 600 mg of rhodium metal are used per kg of cyclic keto-olefins. The catalyst can be recovered by known methods and used again (German Offenlegungsschrift No. 1,954,315 (1969) and German Offenlegungsschrift No. 2,311,388 (1973)).

In the hydroformylation according to the invention, carbon monoxide and hydrogen are in general used in an at least stoichiometric ratio, but preferably in an excess up to 100 mol %. The mixture of carbon monoxide and hydrogen contains carbon monoxide and hydrogen as a rule in a volume ratio of 1:4 to 4:1, in particular in a ratio of 2:1 to 1:2.

The hydroformylation according to the invention is in general carried out within a temperature range of 50° to 200° C. Temperatures within the range of 90° to 180° C. are particularly preferred. The process according to the invention is in general carried out under a pressure of at least 30 bar. The process according to the invention is preferably carried out within a pressure range of 70 to 400 bar.

In general, the process according to the invention is carried out until virtually complete conversion in a time of 20 to 120 minutes.

The process according to the invention is in general carried out in liquid phase. It is here advantageous to fix the catalyst on a solid support, for example silica gel.

The liquid reaction medium can either be a mixture of liquids which are in themselves present (reaction products or excess ligand compound) or, if appropriate, it may also contain an added solvent which does not change under the reaction conditions and in which the catalyst and excess ligand are soluble. Examples of solvents are hexane, octane, cyclohexane, benzene, toluene and xylene.

In a preferred embodiment of the process according to the invention, the hydroformylation of the cyclic keto-olefin to give the cyclic keto-butyraldehyde according to the invention is carried out in the presence of a hydridocarbonyl-phosphine-rhodium complex and in an excess of the phosphine ligand which corresponds to a phosphorus to rhodium ratio of 10 to 80:1, in a hydrocarbon as solvent within a temperature range of 130° to 165° C. and within a pressure range of 150 to 350 bar with hydrogen and carbon monoxide in a ratio of 0.7 to 1.5.

According to the invention, the new cyclic keto-butyraldehydes for the preparation of diisocyanates of the formula (IV)

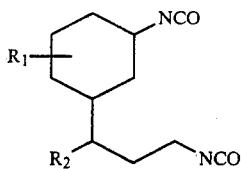

(IV)

in which
R₁ and R₂ have the abovementioned meaning, can be used by reacting the cyclic keto-butyraldehyde in the presence of a hydrogenation catalyst with ammonia and hydrogen within a temperature range of 50° to 280° C. and within a pressure range of 10 to 200 bar to give diamines of the formula (V)

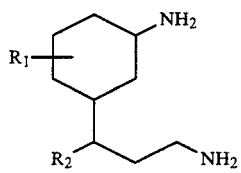

(V)

in which
R₁ and R₂ have the abovementioned meaning, and then treating these diamines in an inert solvent with an acid and reacting the resulting salts within a temperature range of 20° to 250° C. with phosgene.

Diisocyanates of the formula (IV) and diamines of the formula (V) are likewise new.

The reductive amination is in itself known (Houben Weyl, Methoden der Organischen Chemie [Methods of Organic Chemistry], volume 4, part 1/C (1980), pages 412 et seq.).

According to the invention, the diamine is obtained in high selectivity when a molar ratio of ammonia to cyclic keto-butyraldehyde of at least 2.2:1, preferably of 5 to 15:1, is used. The reductive amination can be carried out discontinuously as a liquid-phase hydrogenation or continuously, for example in the trickle phase.

It can be advantageous to use a solvent which is inert under the conditions of the amination according to the invention. Examples of solvents which may be mentioned are alcohols, ethers, amides and heterocyclic compounds, such as methanol, ethanol, isopropanol, butanol, ethylene glycol, ethylene glycol dimethyl ether, tetrahydrofuran, N-methylpyrrolidone, dimethylformamide and hexane. Ethanol and isopropanol are preferred solvents.

In general the reduction amination according to invention is carried out within a temperature range of 50° to 180° C., preferably from 90° to 135° C. The hydrogen pressure should be greater than 10 bar and be within a range of 50 to 200 bar.

It is advantageous to carry out the amination according to the invention with the addition of an ammonium salt, such as ammonium acetate. In this case, 0.1 to 5% of the ammonium salt are in general employed, relative to the keto-aldehyde.

Hydrogenation catalysts for the reductive amination according to the invention in general contain as active components at least one of the metals vanadium, chromium, manganese, iron, cobalt, nickel or copper in a reduced and/or oxidised form. Preferred catalysts are nickel or cobalt catalysts, in the form of supported catalysts, inorganic materials which can be used as supports being kieselguhr, silicic acid, aluminium oxides, silicates, aluminium silicates, montmorillonites, zeolites, spinels, dolomite, kaolin, magnesium silicates, zirconium oxide, iron oxide, zinc oxide, calcium carbonate, silicon carbide, aluminium phosphate, boron phosphate, asbestos or activated carbon and compounds which can be used as organic catalyst supports being naturally occurring or synthetic compounds having a high molecular weight, such as silk, polyamides, polystyrenes, pulp or polyurethanes, it being possible for the supports to be in the form of cakes, ropes, filaments, cylinders, polygons or in the form of a powder.

Preferred catalysts for the amination according to the invention are also catalysts of the Raney type, such as Raney nickel, W-1, W-5, W-6, W-7 Raney nickel (J.Am.Chem.Soc. 69, 3039 (1974)), Raney cobalt catalysts, Raney copper, Raney nickel-iron, Raney cobalt-nickel or Raney cobalt-iron, metal catalysts prepared by the reduction of nickel salts or cobalt salts, such as Urushibara nickel, or nickel salts or cobalt salts reduced by means of metal alkyl compounds, alkali metal hydrides, hydrazine, borates or boron hydride, or catalysts prepared by the reduction of the metal oxides or metal oxide mixtures.

The reduction of the catalysts can also be effected by means of hydrogen, if appropriate at an elevated temperature and under an elevated pressure or under the conditions of the process according to the invention or during the process.

The hydrogenation catalysts can contain as promoters one or more of the following elements in an amount up to 10% by weight: lithium, sodium, calcium, barium, potassium, silver, beryllium, lanthanum, cerium, titanium, vanadium, niobium, tantalum, molybdenum and tungsten. In addition, up to 1% by weight of the elements ruthenium, rhenium, palladium, gold, iridium and platinum can be contained in the hydrogenation catalyst.

Particularly preferred hydrogenation catalysts for the reductive amination according to the invention are Raney catalysts, such as Raney nickel, Raney cobalt and Raney nickel-iron.

The diamine prepared by reductive amination is reacted in a manner which is in itself known with phosgene to give the cyclic diisocyanate. In this step, the diamine, if appropriate in an inert solvent, is reacted with a gaseous acid, such as hydrogen chloride or carbon dioxide, to give the corresponding addition product which is then treated with phosgene.

In general, 2 to 30 mols, preferably 5 to 10 mols, of phosgene are reacted with 1 mol of the diamine.

In this step, the acid is split off and the cyclic diisocyanate is formed. The reaction temperature is in general within the range of 20° to 250° C., preferably 130° to 170° C.

Possible solvents for the phosgenation are all those customary solvents which do not change under the reaction conditions and the boiling point of which is sufficiently high for the phosgenation and which have an adequate boiling point difference to the diisocyanate. Chlorobenzenes, nitrobenzenes, xylenes, tetralin and decalin are preferred. After the solvent has been distilled off, the diisocyanate can be purified in a manner which is in itself known by distillation.

The cyclic diisocyanates according to the invention can be used in accordance with German 2,234,507 (GB 13,51,774) as crosslinking agents in the preparation of polyurethanes which are useful in turn as lacquer additives.

EXAMPLE 1

2,000 g of carvone and 5,000 ml of toluene are reacted at 150° C. and under 280 bar with a 1:1 mixture of hydrogen and carbon monoxide in the presence of 1.3 g of rhodium 2-ethylhexanoate and 152 g of triphenylphosphine in a stainless steel autoclave. After 2 hours no more gas is taken up. The solvent is distilled off under 10 mbar. The residue is fractionated under 0.1 mbar. 1,910 g (80%, relative to the amount of carvone employed) of a mixture are obtained which consists of 80% of 3-(4-methyl-3-oxocyclohex-4-enyl)-butyraldehyde, 15% of 3-(4-methyl-3-oxocyclohexyl)-butyraldehyde and 5% of a saturated oxo alcohol. Boiling point=100°-105° C./0.1 mbar.

The distillation residue contains the hydroformylation catalyst and it can be used for a fresh hydroformylation.

EXAMPLE 2

50 g of carvone, 1.15 g of triphenylphosphine and 0.01 mg of tris-triphenylphosphine rhodium chloride are reacted as described in Example 1 in 250 ml of toluene at 150° C. and under 280 bar for 4 hours with a 1:1 mixture of hydrogen and carbon monoxide. The distillative working-up yields 49 g (82%, relative to the amount of carvone employed) of a mixture (boiling point=101°-105° C./0.1 mbar) which has the same composition as the mixture described in Example 1.

EXAMPLE 3

50 g of dihydrocarvone, 1.5 g of triphenylphosphene and 0.013 g of rhodium 2-ethylhexanoate are reacted as described in Example 1 in 200 ml of toluene at 150° C. and under 280 bar with a 1:1 mixture of hydrogen and carbon monoxide. The distillative working-up yields 51.5 g of 3-(4-methyl-3-oxocyclohexyl)-butyraldehyde (boiling point=98°-100° C./0.1 mbar, 86% of theory).

EXAMPLE 4

100 g of 3-(4-methyl-3-oxocyclohex-4-enyl)-butyraldehyde, 30 g of Raney nickel, 5 g of ammonium acetate and 750 ml of ethanol are introduced into a stirred stainless steel autoclave. The autoclave is sealed and flushed with nitrogen, and 350 ml of liquid ammonia are pumped in. The mixture is heated under 80 bar of hydrogen pressure to 100° C. and the pressure is maintained for 1 hour under 110 bar by means of hydrogen, after the ammonia has been evaporated the catalyst is filtered off from the reaction mixture which has cooled down, and the solvent is distilled off. The distillation yields 76.5 g of 3-(3-amino-4-methylcyclohexyl)-butylamine, boiling point=108°-111° C./0.1 mbar (75% of theory).

EXAMPLE 5

100 g of 3-(3-amino-4-methylcyclohexyl)-butylamine are dissolved in 750 ml of dry chlorobenzene and the resulting solution is saturated at 0° C. with carbon dioxide. The cooling is removed, and while phosgene is being passed in the mixture is heated to the boil. Phosgene is passed in for 8 hours at 150° C. Phosgene which is not reacted is flushed by means of nitrogen from the solution which is now clear. The solvent is distilled off under 10 mbar, and the residue is distilled via a 10 cm Vigreux column. 89.5 g of 3-(3-isocyanato-4-methylcyclohexyl)-butyl isocyanate, boiling point 125°-127° C./0.3 mbar, are obtained.

EXAMPLE 6 (USE EXAMPLE)

The aim was to prepare a polyurethane lacquer from a polyol and a diisocyanate according to the invention.

The polyol used was a polyether which was prepared by reacting trimethylol propane with propylene oxide using alkali metal catalysis and which has a hydroxyl number of 380. 147.4 g of the polyol were mixed with 131.2 g of 3-[3-isocyanato-4-methylcyclohexyl]-butylisocyanate (according to Example 5) with the addition of 0.1% by weight (based on the total weight) of dibutyl tin laurate and applied to a metal foil.

After 8 hours, the surface of the lacquer is not adhesive anymore. After 7 days the lacquer layer is resistant to the solvents toluene, acetone and ethylene glycol diacetate and has high elasticity and scratch resistance.

What is claimed is:

1. A diisocyanate of the formula (IV)

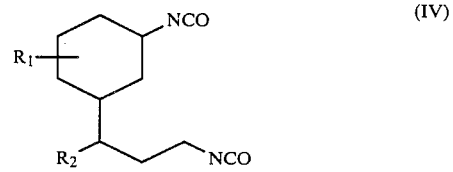

in which $R_1$ and $R_2$ are identical or different and denote hydrogen or lower alkyl and in which the cycloaliphatic ring can contain a double bond.

2. A diisocyanate according to claim 1 in which $R_1$ and $R_2$ are identical or different and denote hydrogen or lower alkyl.

* * * * *